United States Patent
Veeck et al.

(10) Patent No.: US 8,521,248 B2
(45) Date of Patent: Aug. 27, 2013

(54) FIBER-OPTIC PROBE

(75) Inventors: Marcus Veeck, Koblenz (DE); Oliver Goedje, Strasslach (DE); Robert Herz, Rohrdorf (DE); Thomas Thalmeier, Dorfen (DE); Christoph Manegold, Munich (DE); Matthias Bohn, Munich (DE)

(73) Assignee: PULSION Medical Systems SE, Feldkirchen (DE)

( * ) Notice: Subject to any disclaimer, the term of this patent is extended or adjusted under 35 U.S.C. 154(b) by 1043 days.

(21) Appl. No.: 12/583,345

(22) Filed: Aug. 19, 2009

(65) Prior Publication Data
US 2010/0049019 A1    Feb. 25, 2010

(30) Foreign Application Priority Data
Aug. 22, 2008  (EP) .................................... 08162826

(51) Int. Cl.
*A61B 5/1455*  (2006.01)
(52) U.S. Cl.
USPC ......................................... 600/341; 600/342
(58) Field of Classification Search
USPC ................... 600/310, 322, 341, 342; 385/53, 385/103
See application file for complete search history.

(56) References Cited

U.S. PATENT DOCUMENTS

| | | | |
|---|---|---|---|
| 4,226,504 | A | 10/1980 | Bellino |
| 5,673,694 | A | 10/1997 | Rivers |
| 5,995,208 | A | 11/1999 | Sarge et al. |
| 6,954,665 | B2 | 10/2005 | Pfeiffer |
| 2006/0252993 | A1 | 11/2006 | Freed et al. |

FOREIGN PATENT DOCUMENTS
EP    0 336 984    10/1989

OTHER PUBLICATIONS
European Search Report dated Mar. 12, 2009.

*Primary Examiner* — Eric Winakur
(74) *Attorney, Agent, or Firm* — Collard & Roe, P.C.

(57) ABSTRACT

In a fiber-optic probe for intravascular measurements, e.g. oxygen saturation measurements, the fiber-optical core has only two fibers. A single fiber core is also possible. A reinforcement fiber improves stiffness, kink resistance and overall strength of the probe. The reinforcement fiber is arranged essentially parallel to the core fibers. The reinforcement fiber may also be wound around the core in a helical manner thus improving the mechanical properties to an even higher degree. The outside of the sheath is coated with an antithrombogenic coating for reducing the danger of clots forming at the surface. The reinforcement fiber may be made of carbon, metal, ceramics or aramide.

19 Claims, 2 Drawing Sheets

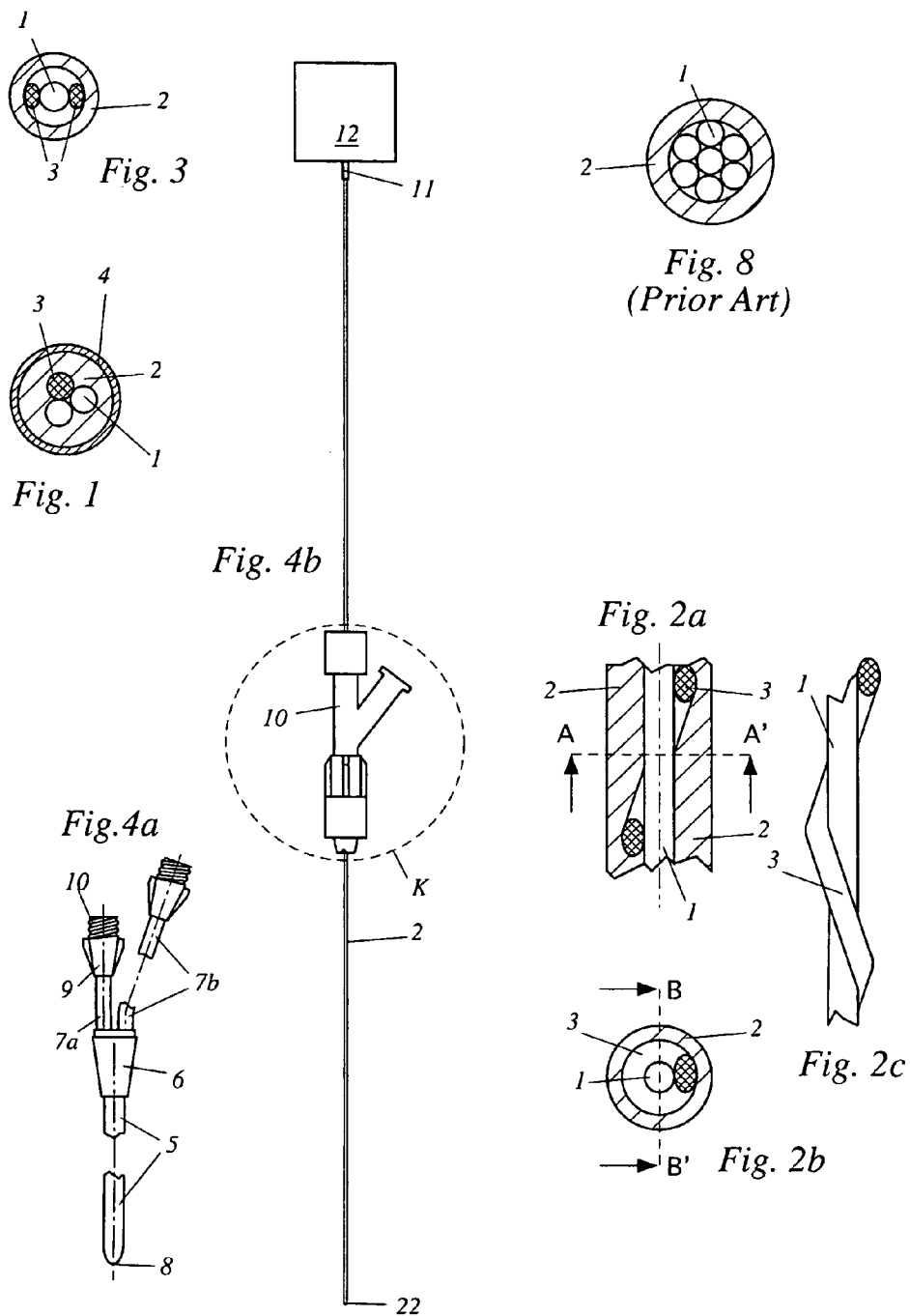

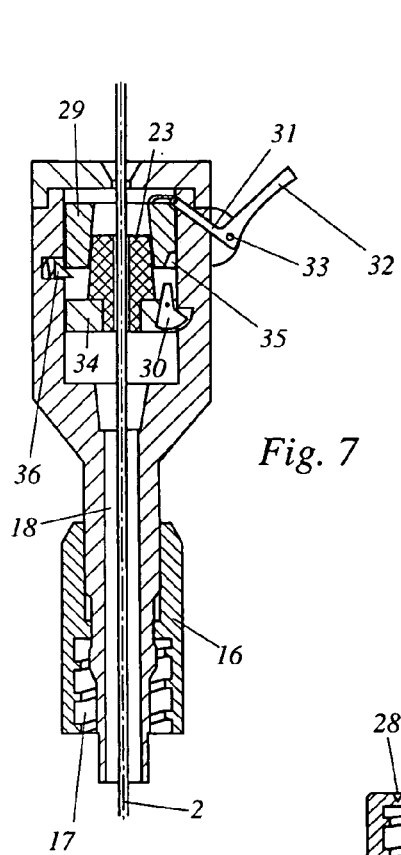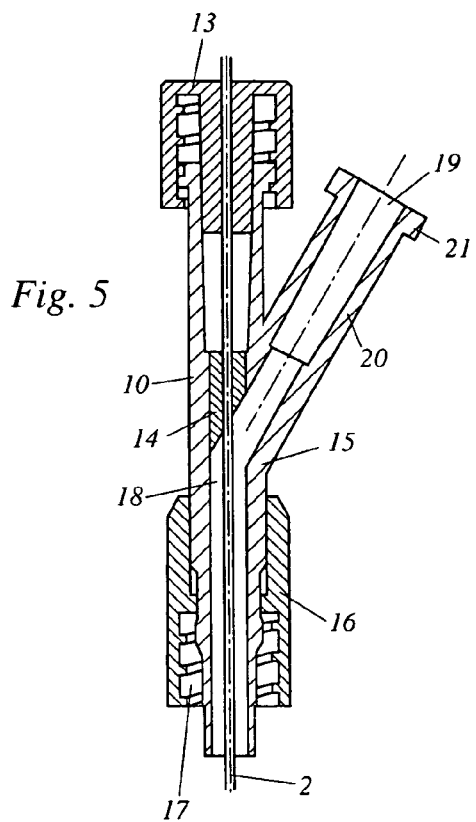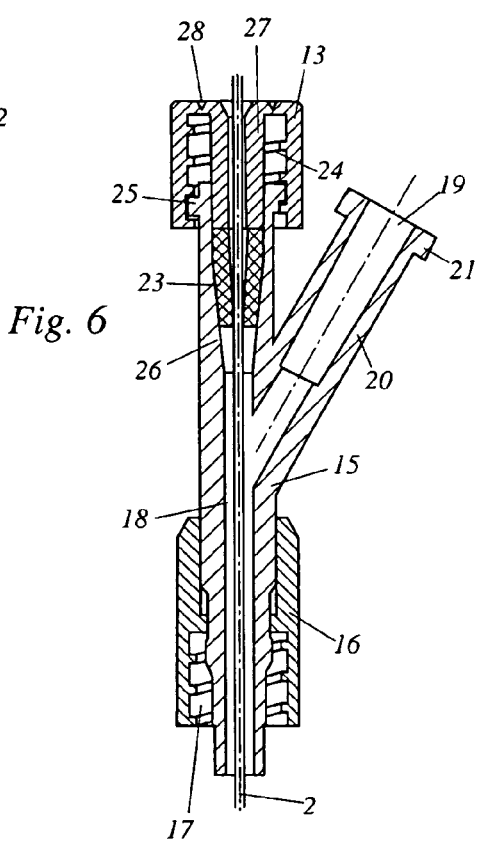

FIBER-OPTIC PROBE

CROSS REFERENCE TO RELATED APPLICATIONS

Applicants claim priority under 35 U.S.C. §119 of European Application No. 08162826.5 filed Aug. 22, 2008.

BACKGROUND OF THE INVENTION

The present invention relates to fiber-optic probes, in particular to fiber-optic probes for intravascular measurements comprising a fiber-optic core for conducting electro-magnetic radiation from a proximal end of said probe to a distal end of said probe and a sheath made of synthetic sheath material and disposed around said core. The present invention further relates to fiber-optic probe assembly comprising such a fiber-optic probe and an intravascular catheter, the latter comprising a probe lumen having a proximal opening and a distal opening and being adapted to accommodate said fiber-optic probe.

Fiber-optic probes of the kind initially mentioned are well-known from the prior art. An important application thereof is the optical in situ measurement of the oxygen saturation of blood, in particular of venous blood.

The centrovenous oxygen saturation (ScvO2) is of particular interest since valuable information about the oxygen availability and oxygen utilization of the entire organism can be obtained from it. A lowering of cardiac output, a reduction of the oxygen carrier hemoglobin, a reduced oxygen supply by artificial respiration or an uncompensated increase in the oxygen consumption of the organism can be quickly detected by continuously monitoring the centrovenous oxygen saturation, which thus is a cost-efficient, global physiological monitoring method. Usually, for centrovenous oxygen saturation in the flowing blood fiber-optic reflecto-oximetry at a measuring wavelength of about 660 nm. Optical radiation of another wavelength, e.g. 930 nm, is used as a reference wavelength. At this wavelength, there is no substantial difference between the reflection of oxygenated and oxygen-free hemoglobin. Parallel measurement at the reference wavelength serves the purpose of compensating flow-dependent and other artifacts.

Fiber-optic probes of the kind initially mentioned may also be used for liver function tests by means of fiber-optic reflection densitometry at a wavelength of about 805 nm after injecting indocyanine green (ICG). In this case, optical radiation at about 900 nm can be used as reference wavelength.

In the surgical field and in intensive medicine, centrovenous catheters (CVC) with several lumina, so-called multilumen CVC, are applied not only to serve for accommodating a fiber optic probe but also to measure the centrovenous pressure, supply infusion solutions, blood and blood derivatives as well as pharmaceuticals via lumnina, and take blood samples for hematological and biochemical analysis.

A catheter system for continuously measuring the centrovenous oxygen saturation is known from the U.S. Pat. No. 5,673,694. It describes a fiber-optic probe of the above type and a fiber-optic catheter with a continuous lumen extending parallel to the fiber-optic lumen for continuous cleansing of the fiber optic in the region of the distal tip. The catheter system has a flexibly adjustable length of the part of the fiber-optic probe inserted in a lumen of the already applied multilumen CVC. Since the fiber-optic probe can be flexibly advanced in its length by means of a frictionally connected locking device, the part of the fiber-optic probe or the fiber-optic catheter, respectively, situated outside of the multilumen CVC must be protected against bacterial contamination by means of a sterile cover.

U.S. Pat. No. 6,954,665 discloses a different way of connecting a fiber-optic probe of the type initially mentioned to a catheter. Therein, the probe is mounted to a Y-shaped connection piece at a fixed length of the probe. The Y-shaped connection piece is fixed to a proximal catheter port, e.g. using a Luer lock system, thus ensuring a predetermined position of the distal end of the probe relative to the catheter tip.

Generally, a small probe diameter is aimed for, as small probe diameters allow the probe lumen and thus the catheter to be designed with a smaller diameter as well in order to decrease the invasiveness of application. On the other hand, a smaller probe diameter usually results in a lower kink resistance. Further, the optical core usually contributes to mechanical stability of the probe to a higher degree than the sheath does, as the core fibers are made of a material stiffer as the sheath material. Therefore, for conventional probes of the above type it is common to provide a fiber-optic bundle to form the fiber-optic core, with multiple core fibers adding to the strength, but also to the diameter.

SUMMARY OF THE INVENTION

It is therefore an object of the present invention to achieve a high kink resistance at a small probe diameter for the type of probes initially mentioned.

According to one aspect of the present invention, this object is achieved by a fiber-optic probe for intravascular measurements comprising a fiber-optic core for conducting electro-magnetic radiation from a proximal end of said probe to a distal end of said probe and a sheath made of synthetic sheath material and disposed around said core. The fiber-optic probe comprises at least one reinforcing fiber made of material different from the material of which the fiber-optic core is made. This allows selecting the material of the reinforcing fiber focusing on mechanical properties thereof. In other words, optical and mechanical functions can be allocated to separate elements of the probe, thus adding a degree of freedom and facilitating optimization of the respective material properties.

Advantageously, the material of said reinforcing fiber may be carbon, metal (e.g. a titanium wire or steel wire), ceramics or aramide.

Due to reinforcement, the fiber-optic core may advantageously be comprised of a single optical fiber or two optical fibers reducing probe diameter yet achieving satisfactory strength of the probe.

According to one preferred embodiment, the fiber-optic core may be split in two single core fibers with at least one reinforcing fiber disposed between said single core fibers.

To further increase kink resistance, one or more reinforcing fibers may advantageously be wound around part of the core or the entire core in a helical manner.

For operation, the probe may advantageously comprise coupling means for coupling the fiber-optic probe to an electro-magnetic radiation source means, e.g. an LED source or laser source, and to electromagnetic radiation detection means, wherein the coupling means are adapted for guiding efferent electro-magnetic radiation from the electro-magnetic radiation source means to the fiberoptic core and for guiding afferent electro-magnetic radiation from the fiber-optic core to the electro-magnetic radiation detection means.

Preferably, the fiber-optic probe comprises locking means for locking the fiber-optic probe to a fitting counterpart.

Therein, according to a preferred embodiment, the locking means are permanently fixed to the sheath at a predetermined axial position thereof.

Preferably, the sheath comprises at least one visible mark indicating an axial position for facilitating defined axial placement. Visible marks may include, e.g., visible rings, letters or symbols, zones of different colors and the like.

Advantageously, the sheath is coated with a coating material different from said sheath material. Such a coating material may be selected to achieve preferred surface properties, especially properties avoiding blood clotting and other undesired phenomena when in clinical use.

When forming an assembly of a fiber-optic probe according to the present invention with an intravascular catheter, the latter comprises a probe lumen having a proximal opening and a distal opening for accommodating the fiber-optic probe.

Preferably, the axial length of the probe from the proximal end to the distal end is longer than the length of the probe lumen from the proximal opening to the distal opening. This ensures that the tip of the probe will be disposed in free blood flow.

According to one particularly advantageous embodiment, the catheter comprises at least one additional lumen, which may be used for measuring the centrovenous pressure, supplying infusion solutions, blood and blood derivatives as well as pharmaceuticals, or taking blood samples for hematological and biochemical analysis.

The assembly may advantageously comprise electromagnetic radiation source means, e.g. a laser or laser diode or one or more LEDs and electro-magnetic radiation detection means.

The electro-magnetic radiation detection means may advantageously comprise one or more photodiodes. In a particularly preferred embodiment the detection means may comprise photometer means. By analysis of the wavelength information a wider variety of physiological parameters may be susceptible to measurement. According to a particularly preferred embodiment, the electro-magnetic radiation source means comprise a broadband, e.g. white light, light source.

Advantageously evaluation means, preferably computer means with digital signal processing capabilities, are linked to said electro-magnetic radiation detection means.

Preferably, the evaluation means are adapted to determine an oxygen saturation from measurement readings received from the electromagnetic radiation detection means in response to emission of electro-magnetic radiation by the electro-magnetic radiation source.

According to one preferred embodiment, fixing of the fiber optic probe to the catheter may be performed by using a fixed connecting piece as known per se from the prior art.

According to a particularly preferred embodiment, the fiber-optic probe assembly further comprises fixing means for fixing the fiberoptic probe in an axial position relative to the catheter, and the fixing means are manually shiftable from a loose position to a fixed position but not manually shiftable back from the fixed position to the loose position, wherein the axial position of the fiber-optic probe relative to the catheter is manually adjustable when the fixing means are in the loose position and the axial position of said fiber-optic probe relative to said catheter is not manually adjustable when said fixing means are in said fixed position. Such a setup allows initially adjusting the length of the probe. Once the probe has been fixed in the fixed position, as shifting the fixing means to the fixed position is irreversible, the probe cannot inadvertently be pulled back out of the blood flow. Further, infiltration of contaminations is avoided, as the probe part exposed to the surroundings cannot be pushed into the lumen, once the fixed position has been reached.

Fixing means which are manually shiftable from a loose position to a fixed position but not manually shiftable back from the fixed position to the loose position can be designed in may ways, for example by using a tightening screw system with a chain-saw thread, one-way clamping or one-way clip systems, tightening means or locking means with a shear-off operating member or the like. A shear-off operating member (tightening grip, lever or the like) is constructed such that it either shears off during the locking or tightening procedure once a certain locking or tightening stage has been reached, or it shears off when trying to reverse the locking or tightening procedure In a particularly preferred embodiment, the fixing means comprise means for limiting forces exerted upon the fiber-optic probe to a maximum value preventing probe damage when the fixing means are shifted from the loose position to the fixed position. In order to implement this, tightening means or locking means with a shear-off operating member as described above may be employed. Further, limited clamping forces can also be achieved by employing resilient clamping elements (such that the fiber-optical) probe is held by restoring forces of the deformed resilient clamping elements) and limiting the deformation of the resilient elements by suitable geometrical conditions. As resilient material usually exhibits increasing restoring forces the more it is deformed, limiting deformation will result in limiting restoring forces.

In an advantageous embodiment, advancing means are provided for advancing the fiber-optic probe a predetermined distance relative to the catheter, wherein the advancing means are operable by shifting the fixing means from the loose position to the fixed position. This allows inserting the probe until the tip of the probe approximately reaches the distal opening of the probe lumen and then shifting the fixing means from the loose position to the fixed position, wherein the tip of the probe is advanced a defined distance into the blood stream. It is thus possible to insert the probe into a catheter already applied to a patient until a measurement signal indicates that the distal tip of the probe is in contact with patient's blood and then perform the fixing procedure as indicated above.

It is to be noted that the above features of fixing the probe relative to the catheter in an irreversible manner, wherein preferably the forces exerted upon the fiber-optic probe are limited and preferably a predefined advancement of the probe is provided, may also be very advantageous in connection with conventional probes.

Generally, any of the embodiments described or options mentioned herein may be particularly advantageous depending on the actual conditions of application. Further, features of one embodiment may be combined with features of another embodiment as well as features known per se from the prior art as far as technically possible and unless indicated otherwise.

BRIEF DESCRIPTION OF THE DRAWINGS

The invention and preferred embodiments thereof will now be described in more detail. The accompanying drawings, which are schematic illustrations, serve for a better understanding of the features of the present invention.

The drawings are schematic and not true to scale. Corresponding features are marked with the same respective reference numerals in the various drawings.

Therein,

FIG. 1 shows a cross-sectional view of a fiber-optic probe with two optical fibers and one reinforcement fiber, FIG. 2a shows part of a longitudinal sectional view of a fiber-optic probe with one optical fiber and a helical reinforcement fiber, wherein part of the sheath material is broken away to allow view on the reinforcement, and wherein fiber the section plane is indicated as line B-B' in FIG. 2b with the arrows indicating the viewing direction, FIG. 2b shows a cross-sectional sectional view of the fiber-optic probe of FIG. 2a with part of the sheath material broken away to allow view on the reinforcement fiber, wherein the section plane is indicated as line A-A' in FIG. 2a with the arrows indicating the viewing direction, FIG. 2c shows a longer part of the fiber optic-core and the helical reinforcement fiber of FIG. 2a, wherein the sheath material is not shown for illustrative purposes, FIG. 3 shows a cross-sectional view similar to FIG. 2a, wherein, however, two reinforcement fibers are provided, FIG. 4a shows a dual-lumen, dual-port catheter being part of a fiber-optical probe assembly according to the invention, wherein the long body parts are depicted in a broken, interrupted manner, FIG. 4b shows a view of a fiber-optic probe according to the invention, which is attached to a light source and light detecting device, FIG. 5 shows a partial view in longitudinal sectional view, indicated by a broken circle K in FIG. 4b, which essentially contains a connecting piece, for connecting the probe to a catheter like the one shown in FIG. 4a, that is securely attached to the fiber-optic probe as per se known from the prior art, FIG. 6 shows a longitudinal sectional view of an alternative connecting piece with resilient clamping member and a shear-off tightening nut to reduce clamping force and allow irreversible clamping of a slide-in fiber-optical probe, FIG. 7 shows a longitudinal sectional view of another alternative connecting piece with resilient clamping member and an irreversible fixing mechanism that also advances the fiber-optical probe during the fixing procedure, and FIG. 8 shows a cross-sectional view of a conventional fiber-optical probe with a fiber-optical bundle constituting the fiber-optical core.

DETAILED DESCRIPTION OF THE EMBODIMENTS

The conventional probe shown in FIG. 8 has a fiber-optical bundle constituting the fiber-optical core 1. The core comprises both efferent fibers for guiding light from a light source (not shown) to the distal tip of the probe and afferent fibers for guiding reflected, scattered or fluorescent light from the distal tip of the probe to detecting means (not shown) connected with the probe. The core 1 is protected by a sheath 2. Due to the rather large probe diameter, kinking resistance is acceptable.

FIG. 1 shows a small diameter probe according to the present invention wherein the fiber-optical core 1 comprises only two fibers. A reinforcement fiber 3 improves stiffness, kink resistance and overall strength of the probe. The reinforcement fiber 3 is arranged essentially parallel to the core fibers 1. The outside of the sheath 2 is coated with an anti-thrombogenic coating 4 for reducing the danger of clots forming at the surface. The coating 4 may be comprised, for example, of PTFE or another suitable material.

The probe depicted in FIGS. 2a-c comprises a single fiber core 1 allowing particularly small probe diameters. The single fiber serves to guide both efferent and afferent radiation. The reinforcement fiber 3 is wound around the core 1 in a helical manner thus improving stiffness and overall strength of the probe. The material of the core 1 and sheath 2 can be chosen without having to worry to much about the mechanical properties thereof. The section plane of FIG. 2a is indicated as line B-B' in FIG. 2b and the section plane of FIG. 2b is indicated as line A-A' in FIG. 2a with the arrows indicating the viewing direction.

FIG. 3 shows a single fiber probe similar to FIGS. 2a-c. However, two helical reinforcement fibers 3 are wound around the core 1 providing even further improved stiffness and strength of the probe.

The catheter shown in FIG. 4a is intended for accommodating a fiber-optic probe according to the present invention and has a flexible, elongated, centrovenously applicable basic body 5, in which two lumina are formed. The lumina extend further proximally above a branching 6 in two extensions 7a, 7b. The probe lumen (not visible), whose inside diameter is larger than the outside diameter of the fiber-optic probe, extends from the distal end 8 of the basic body 5 of the catheter through it and further through the extension 7a to a distal port. The distal port comprises a counterpart 9 for a connecting piece 10 for connecting the fiber-optic probe to the catheter. The counterpart 9 is firmly connected with the basic body 5 via the extension 7a and the branching 4. The counterpart 9 has an external thread 9 via which the connecting piece 10 can be securely attached.

FIG. 4b shows a fiber-optic probe with an internal structure as described in FIGS. 1-3 or similar. The probe is connected via proximal coupling means 11 to a joint light source and measuring device 12 comprising electro-magnetic radiation source means and electromagnetic radiation detection means.

The fiber-optic probe shown in FIG. 4b is suitable for the measurement of the centrovenous oxygen saturation. The light source and measuring device 12 is constructed for the simultaneous emission and measurement of radiation of the measuring wavelength of 660 nm and the reference wavelength. At this wavelength, the reflection properties of oxygenated and oxygen-free hemoglobin in the blood differ quite substantially. The reference wavelength is e.g. 880 nm, since at this wavelength there is no substantial difference of the reflection between oxygenated and oxygen-free hemoglobin in the blood. The centrovenous oxygen saturation is calculated with reference to the ratio between reflection measurements at the measuring wavelength and the reference wavelength with the aid of computer-implemented algorithms known from the literature and technology. Alternative implementation of a white light source and photometer means will allow photometric evaluation of various wavelength and thus analysis of other chemical compounds susceptible to photometric methods.

FIG. 5 shows the connection piece 10 in detail. This type of connection piece is per se known from the prior art.

The connecting piece 10, shown in cross section in FIG. 5, is firmly glued together with the sheath 2 of the fiber-optic probe. It consists of four parts 13, 14, 15, 16 glued together, wherein at least the end part 13 is glued to the fiber-optic probe. The guide part 14 stabilizes the probe in the connecting piece 10. The threaded part 16 has an internal thread 17 via which the connecting piece 10 can be attached to the counterpart 9 of the catheter. In the connected state, the probe lumen continues on the inside 18 of the Y-part 15 of the connecting piece 10. The probe lumen is then tightly sealed proximally by means of the end piece 13.

The inside 18 of the Y-part 15 continues in the cleansing channel 19 which runs through the cleansing connection 20 which is molded onto the Y-part 15 and ends in a flange 21. The cleansing channel 19 can be sealed at the flange 21; in addition, a cleansing device (not shown) can be attached here, so that the probe lumen can be cleansed via the inside 18 of the Y-part 15.

In this configuration, the probe is inserted into the catheter through the counterpart 9 and the probe lumen. The length of the probe and the probe lumen and the distance between the connection piece 10 and the distal tip 22 of the probe need to be adapted to each other in order to make sure that the distal tip 22 of the probe slightly protrudes from the distal end 8 of the basic body 5 of the catheter. Insertion of the probe and connecting the connection piece 10 to the counterpart 9 are a joint procedure in this configuration.

FIGS. 6 and 7 show alternative configurations of the connection piece. Both configurations allow inserting the probe after connecting the connection piece to the counterpart 9 of the catheter. Therefore, the probe length can be arbitrary (provided that it is significantly longer than the probe lumen and the extension thereof in the interior 18 of the connection piece.

The connection piece configurations of FIGS. 6 and 7 are also suitable for conventional probes as known from the prior art.

In FIG. 6, the probe extends through a resilient clamping member 23. By turning the tightening nut 13, the thread 24 of the nut 13 and the matching thread 25 of the Y-part 15 cause the center part 27 of the nut 13 to advance and thus push the clamping member 23 to advance into the conical part 26 of the interior 18 of the Y-part 15. In the conical part 26, the resilient clamping member 23 is pushed together to tightly hold the probe. Once a predetermined tightening force is reached, the thread 24 will shear off from the center part 27 of the nut 13 due to the circumferential groove 28. Without applying tools it is hardly possible to remove the clamping member 23 after tightening. Therefore, fixing the probe is irreversible in this configuration. As, after fixing, the probe can neither be removed nor further advanced into the probe lumen, the risk of channeling contaminating germs into the probe lumen is reduced, and inadvertent removal of the distal tip 22 of the probe from the blood flow is avoided.

Though FIG. 7 does not show a cleansing channel 19, it will be readily perceived that it can be easily implemented in a manner analogous to FIGS. 5 and 6.

In FIG. 7, the probe also extends through a resilient clamping member 23. The outside of the clamping member 23 is conical in a manner matching the conical inside of the piston 29. First, the clamping member 23 is held in its position by the carriage 34 and an interlock 30 provided therein. When the lever 31 is rotated around the hinge 33 by pushing the operating element 32, the lever 31 will push the piston towards the resilient clamping member 23 causing the latter to tighten around the probe. After advancing a predetermined distance, a slant groove 35 in the piston 29 will cause the interlock 30 to release and the carriage 34 and the probe are advanced together for a predetermined distance until the operating element 32 reaches the cover part 13 of the connection piece. The resiliently supported sawtooth lock 36 prevents the piston 29 from moving back. Therefore, fixing the probe is irreversible in this configuration as well.

This allows inserting the probe until the distal tip 22 of the probe approximately reaches the distal opening of the probe lumen near the catheter tip 8 and then pushing the operating element 32 from the loose position to the fixed position, wherein the tip 22 of the probe is advanced a defined distance into the blood stream. It is thus possible to insert the probe into the catheter already applied to a patient until a measurement signal indicates that the distal tip 22 of the probe is in contact with patient's blood and then perform the fixing procedure as indicated above.

What is claimed is:

1. A fiber-optic probe for intravascular measurements comprising a fiber-optic probe for intravascular measurements said fiber optic probe comprising core with no more than two optical fibers made of a first material for conducting electromagnetic radiation from a proximal end of said probe to a distal end of said probe,
   wherein said fiber-optic probe comprises at least one reinforcing fiber made of a second material different from said first material of which the fiber-optic core is made, said second material selected from the group consisting of carbon, metal, ceramics and aramide, and
   wherein said fiber-optic probe assembly further comprises an intravascular catheter, said catheter comprising a probe lumen having a proximal opening and a distal opening and being adapted to accommodate said fiber-optic probe,
   wherein said fiber-optic probe assembly further comprises a sheath made of synthetic sheath material and disposed around said core and said reinforcing fiber so as to be in direct contact with said reinforcing fiber, and
   wherein the axial length of said probe from said proximal end to said distal end is longer than the length of said probe lumen from said proximal opening to said distal opening.

2. The fiber-optic probe assembly according to claim 1, wherein said fiber-optic core is composed of a single optical fiber.

3. The fiber-optic probe assembly according to claim 1, wherein said fiber-optic core is composed of two optical fibers.

4. The fiber-optic probe assembly according to claim 1, wherein said fiber-optic core is split into two single core fibers with at least one of said at least one reinforcing fibers disposed between said single core fibers.

5. The fiber-optic probe assembly according to claim 1, wherein at least one of said reinforcing fibers is wound around at least part of the core in a helical manner.

6. The fiber-optic probe assembly according to claim 1, further comprising a coupling device for coupling said fiber-optic probe to an electro-magnetic radiation source and to an electromagnetic radiation detector, said coupling device being adapted for guiding efferent electro-magnetic radiation from said electro-magnetic radiation source to said fiberoptic core and for guiding afferent electro-magnetic radiation from said fiber-optic core to said electro-magnetic radiation detector.

7. The fiber-optic probe assembly according to claim 1, further comprising a locking device for locking said fiber-optic probe to a fitting counterpart.

8. The fiber-optic probe assembly according to claim 7, wherein said locking device is permanently fixed to said sheath at a predetermined axial position thereof.

9. The fiber-optic probe assembly according to claim 1, wherein said sheath comprises at least one visible mark indicating an axial position for facilitating defined axial placement.

10. The fiber-optic probe assembly according to claim 1, wherein said sheath is coated with a coating material different from said sheath material.

11. The fiber-optic probe assembly according to claim 1, wherein said catheter comprises at least one additional lumen.

12. The fiber-optic probe assembly according to claim 1, further comprising an electromagnetic radiation source and an electro-magnetic radiation detector.

13. The fiber-optic probe assembly according to claim 12, wherein said electro-magnetic radiation detector comprises a photometer.

14. The fiber-optic probe assembly according to claim 12, wherein said electro-magnetic radiation source comprises a broadband light source.

15. The fiber-optic probe assembly according to claim 12, further comprising an evaluation device linked to said electro-magnetic radiation detector.

16. The fiber-optic probe assembly according to claim 15, wherein said evaluation device is adapted to determine an oxygen saturation from measurement readings received from said electromagnetic radiation detector in response to emission of electro-magnetic radiation by said electro-magnetic radiation source.

17. The fiber-optic probe assembly according to claim 12, wherein said fiber-optic probe assembly further comprises a fixing device for fixing said fiberoptic probe in an axial position relative to said catheter, and said fixing device is manually shiftable from a loose position to a fixed position but not manually shiftable from said fixed position to said loose position, wherein the axial position of said fiber-optic probe relative to said catheter is manually adjustable when said fixing device is in said loose position and the axial position of said fiber-optic probe relative to said catheter is not manually adjustable when said fixing device is in said fixed position.

18. The fiber-optic probe assembly according to claim 17, wherein said fixing device comprises a limiting device for limiting forces exerted upon said fiber-optic probe to a maximum value preventing probe damage when said fixing device is shifted from said loose position to said fixed position.

19. The fiber-optic probe assembly according to claim 17, further comprising an advancing device for advancing the fiber-optic probe a predetermined distance relative to the catheter, wherein said advancing device is operable by shifting said fixing device from said loose position to said fixed position.

* * * * *

UNITED STATES PATENT AND TRADEMARK OFFICE
CERTIFICATE OF CORRECTION

PATENT NO. : 8,521,248 B2  
APPLICATION NO. : 12/583345  
DATED : August 27, 2013  
INVENTOR(S) : Veeck et al.

Page 1 of 1

It is certified that error appears in the above-identified patent and that said Letters Patent is hereby corrected as shown below:

In the Claims

In Column 8, line 6 (line 1 of Claim 1) after "probe" please change "for intravascular measurements" to correctly read: --assembly--.

In Column 8, line 7 (line 2 of Claim 1) after "measurements" please insert: --,--.

In Column 8, line 8 (line 3 of Claim 1) after "comprising" please insert: --a fiber-optic--.

Signed and Sealed this  
Twenty-fourth Day of December, 2013

Margaret A. Focarino  
*Commissioner for Patents of the United States Patent and Trademark Office*